United States Patent [19]

Iris

[11] Patent Number: 4,855,131
[45] Date of Patent: Aug. 8, 1989

[54] PHYTOPREPARATION FOR TREATING SKIN AFFECTIONS

[75] Inventor: Pasini Iris, Crevalcore, Italy

[73] Assignee: IRIS S.a.s. di Salvioli Michele e C., Soliera, Italy

[21] Appl. No.: 203,910

[22] Filed: Jun. 8, 1988

[30] Foreign Application Priority Data

Jun. 30, 1987 [IT] Italy ................. 21115 A/87

[51] Int. Cl.⁴ ............ A61K 7/06; A61K 35/78
[52] U.S. Cl. .................. 424/74; 424/195.1; 514/844; 514/847; 514/861; 514/863; 514/864; 514/880; 514/881
[58] Field of Search .......... 424/74, 195.1; 514/844, 514/847, 880, 881, 861, 863, 864

[56] References Cited

U.S. PATENT DOCUMENTS 4,569,839 2/1986 Grollier et al. ................. 514/844

FOREIGN PATENT DOCUMENTS

| 3533121 | 4/1986 | Fed. Rep. of Germany ... 424/195.1 |
| 2416010 | 10/1979 | France ................. 514/880 |
| 0148716 | 8/1984 | Japan ................. 424/195.1 |
| 1986 | 5/1881 | United Kingdom ............. 424/195.1 |

OTHER PUBLICATIONS

Back, *The Illustrated Herbal*, pp. 16, 67–69, 83–84, 87–90, 104–105, 109–110, 118–120, 154–157, 1987.
Lust, *The Herb Book*, pp. 111, 247, 269–271.

*Primary Examiner*—John W. Rollins
*Assistant Examiner*—Wendy Catchpole
*Attorney, Agent, or Firm*—Finnegan, Henderson, Farabow, Garrett & Dunner

[57] ABSTRACT

The present invention relates to a preparation for the treatment of skin or scalp affections, with an exclusively plant basis, obtained by infusion in vinegar of Geum, Lavandula, Mentha, Allium, and Salvia, preferably with the addition of other plant substances having a calmative or aroma-giving action; the preparation has shown itself to be outstandingly efficacious in impeding certain conditions which promote loss of hair.

11 Claims, No Drawings

PHYTOPREPARATION FOR TREATING SKIN AFFECTIONS

The present invention relates to a preparation for the treatment of the hair and skin, which has shown singular efficacy in various types of skin pathology, in particular psoriasis, both of the skin generally and localized on the scalp, as also furfuraceous seborrhea; it is useful generally in skin pathologies giving rise to loss of hair.

In the case of diffused loss of hair, of varying degree, the first and simplest cause to look for is postinfective defluvium.

The prognosis for defluvium is always favourable, with complete normalization. Violent traumas (car accident, etc.), surgery, severe fractures, can be followed by hair loss within 2 or 3 months. Such hair loss is almost in every case spontaneously reversible over time.

It has currently become apparent that alopecias, after prolonged treatment with corticosteroids and cytostatic drugs (these last blocking the intense cellular mitotic activity of the hair bulb), occur with relative frequency.

The reversibilty of such alopecias depends on the damage suffered by the bulb cells as a result of the more or less prolonged use of the said drugs.

An important cause of hair loss is seborrheic alopecia, which occurs chiefly in males, often in youth (even before twenty years of age), the presenting signs being thinning hair and progressive hair loss.

The defluvium is usually preceded and/or accompanied by much scurf, which is initially dry and then greasy. By stages, the subject reaches the stage of baldness characterized by what is known as "professor angles"; this is currently attributed to androgynous incretion in genetically predisposed subjects.

The preparation according to the invention is essentially composed of an infusion in vinegar of:

Geum, Lavandula, Mentha, Allium and Salvia, preferably with the addition of other plant substances possessing calmative action.

Use can in particular be made, to produce the said calmative action, freshening and aroma giving action of the preparation, of the following: Citrus, Ocimum, Crataegus, Lippia, Iris, Rosa, Tilia, Verbena, Urtica, Juniperus.

The use of the plants mentioned above is not in general critical: use can also be made of *Geum urbanum* (herb bennet), *L. vera* (Lavender), *Mentha pulegium* (Mint), *Allium porro* (Leek), *Allium sativum* (Garlic), *Salvia officinalis* (Sage), *Citrus aurantium* (Bitter orange peel), *Citrus limonum* (Lemon peel), *Ocimum basilicum* (Sweet basil), *Crataegus oxyacantha* (Hawthorn), *Lippia citriodora* (Fogfruit), *Iris florentina* (Orris), *Rosa canina* (Rose hips), *Tilia silvestris* (Lime), *Verbena officinalis* (Verbena), *Urtica diorca urens* (Nettle), *Juniperus communis* (Juniper berries).

The plant components are used in the infusion in weight ratios defined by the following ranges, referred to one litre of vinegar:

Geum—5 to 10 g
Lavandula—5 to 10 g
Mentha—8 to 20 g
Allium—20 to 50 g
Salvia—10 to 30 g The weights of the plant components should be understood as measured for plants in the natural state, freshly picked.

The vinegar used for the infusion should be obtained, either exclusively or in a largely prevalent part, by acetification of wine. The total acidity should be in the pH range 2.5 to 5.

The infusion requires cold immersion of the plant components for a period of time variable from 15 to 50 days.

The infusion is then filtered, and to obtain the final preparation in the form of a lotion it is diluted with distilled water (10 to 20%), with optional addition of perfumed natural substances.

If it is wished to obtain a creamy preparation, suitable for localized treatment of the skin, the infusion can in general be emulsified with natural oils, employing the usual technology for preparing stable cream preparations.

The most important factor is that the lotion is a phytocomplex, i.e. an exclusively plant based preparation, and does not interfere with endogenous metabolisms; for this reason it can be used unreservedly, having no contraindications.

Application of the lotion not only prevents all the different exogenous anomalies which lead to hair bulb atrophy, but, as a result of its freshing and detoxicating activity, assists the gradual restoration of a notoriously deteriorated environment such as that of human hair.

The preparation according to the invention has been found devoid of acute toxicity, both after skin application and also in animal oral toxicity studies. Application of the product to the skin, repeated even daily for prolonged periods of time, has shown patient-tolerance to be excellent and in no case caused symptoms or other signs of toxicity of any kind.

Some examples of preparations according to the invention are given below.

EXAMPLE 1

In 1 litre of vinegar from wine, the underlisted amounts of plants, freshly picked and weighed in such condition, were infused.

The parts of the plants used were root, stems, leaves and flowers.

*Citrus aurantium*—3 g
*Ocimum basilicum*—4 g
*Crataegus oxyacantha*—8 g
*Geum urbanum*—10 g
*Lippia citroiodora*—5 g
*Iris florentina*—3 g
*Citrus limonum*—5 g
*L. vera*—10 g
*Mentha pulegium*—15 g
*Rosa canina*—2 g
*Allium porrum*—30 g
*Tilia silvestris*—3 g
*Verbena officinalis*—10 g
*Salvia officinalis*—25 g The preparation under infusion was allowed to stand cold (15° C.) for 20 days; the infusion was then filtered, diluted with 10% of distilled water.

A sample of 50 outpatients in the age range of 22 to 44 years were treated with the preparation. The sample was deliberately homogeneous, in that thinning hair occurs in the age range in question. The subjects examined were all given the normal biohumoral screening tests; a group of 15 subjects had a trichogram made, the remainder followed a diet. The sole exception was the group (seven female patients) with a neurogenous alopecia and in these cases the treatent with the preparation according to the invention was combined with pharmacological therapy with benzodiazepin. Lastly, telethermography was performed.

The lotion (in ampoules) was applied by rubbing onto the wet hair after washing with a neutral shampoo, three times a week for 30 days.

Thereafter the lotion was applied twice a week.

At the three-monthly controls, the cases of thinning hair showed distinct improvement.

Particularly evident was an improvement in the condition of the hair bulbs (disappearance of bulb atrophy) and in the vitality of the hair shafts.

In the five cases of "professor angles" baldness, a certain proliferation of the hair follicles was noted, with appearance of growing hair. This may find explanation in the possibility that the lotion directly stimulates the hair follicle to broaden, and the broader the follicle the longer and thicker is the hair that it produces.

Telethermography evidenced an increase in blood flow in the skin area to which the lotion was applied; such increase may be necessary to broaden the follicles.

EXAMPLE 2

The underlisted amounts of plants, freshly picked and then weighed, were infused in 1 litre of vinegar from wine. The parts of the plants used were the roots, leaves, stems and flowers.

*Citrus aurantium*—4 g
*Crataegus oxyacantha*—3 g
*Geum urbanum*—8 g
*Iris florentina*—1 g
*Citrus limonum*—4 g
*L. vera*—10 g
*Mentha pulegium*—12 g
*Rosa canina*—3 g
*Allium porrum*—25 g
*Salvia officinalis*—20 g The preparation under infusion was allowed to stand cold (15° C.) for 25 days; the infusion was then filtered and a lotion prepared as in Example 1, with comparable results.

EXAMPLE 3

The underlisted amounts of plants, freshly picked and then weighed, were infused in 1 litre of vinegar from wine. The parts of the plants used were as specified above.

*Urtica diorca urens*—10 g,
*Citrus aurantium*—2 g,
*Geum urbanum*—7 g,
*Citrus limonum*—3 g,
*L. vera*—12 g,
*Mentha pulegium*—12 g,
*Allium sativum*—30 g,
*Verbena officinalis*—5 g,
*Salvia officinalis*—30 g,
*Juniperus communis*—5 g.

The preparations being infused was allowed to stand cold (15° C.) for 35 days; the infusion was then filtered, emulsified with vegetable oils (2%), with addition of iodine (1%). The preparation in the form of a cream was efficacious in treating body skin psoriasis. A similar preparation can be obtained as a gel or as a liquid, by omitting the emulsification.

On the basis of what has been set forth herein, various formulations can be adopted to obtain particular effects with the preparation, especially as regards its freshening and aroma-giving components, without for this reason going beyond the scope of the present invention.

I claim:

1. A composition for the treatment of skin and scalp affections consisting essentially of an infusion in vinegar of the indicated amounts of the following freshly picked plant components, all amounts being with respect to one litre of vinegar:

Geum—5 to 20 grams;
Lavandula—5 to 15 grams;
Mentha—8 to 40 grams;
Allium—10 to 60 grams; and
Salvia—10 to 30 grams;

all of the above amounts being the weights of the plants as freshly picked.

2. The composition of claim 1, wherein said vinegar is wine vinegar.

3. The composition of claim 1, further including one or more plant substances selected from the group consisting of Citrus, Ocimum, Crataequs, Lippia, Iris, Rosa, Tilia, Verbena, Urtica, and Juniperus, providing calmative or aroma-giving actions.

4. The composition of claim 1, wherein said plant components are present in the following amounts:

Geum—5 to 10 grams;
Lavandula—5 to 10 grams;
Mentha—8 to 40 gams;
Allium—30 to 50 grams; and
Salvia—15 to 25 grams.

5. The composition of claim 1, wherein said Geum is *Geum urbanum,* said Lavandula is *Lavandula vera spica,* said Mentha is *Mentha pulegium,* said Allium is *Allium porrum* or *sativum,* and said Salvia is *Salvia officinalis.*

6. The composition of claim 1, wherein the pH of said composition is in the range of 2.5 to 5.

7. The composition of claim 1 which has been diluted with distilled water.

8. The composition of claim 1 which has been emulsified with a natural oil.

9. The composition of claim 5, further including *Citrus aurantium, Ocimum basilium, Crataequs oxyacantha, Lippia citroiodora, Iris florentina, Citrus limonium, Rosa canina, Tilia silvestris,* and *Verbena officinalis* and which has been diluted with distilled water.

10. The composition of claim 5 further including *Citrus aurantium, Crataequs oxycantha, Iris florentina, Citrus limonium* and *Rosa canina* which has been diluted with distilled water.

11. The composition of claim 5, further including *Urtica diorca urena, Citrus aurantium, Citrus limonium, Verbena officinalis* and *Juniperus communis* and which has been emulsified with vegetable oil.

* * * * *